(12) United States Patent
Veeger et al.

(10) Patent No.: US 9,155,692 B2
(45) Date of Patent: Oct. 13, 2015

(54) ESSENTIALLY WATER-FREE PERSONAL CLEANSER CONTAINING ETHYL CELLULOSE

(71) Applicant: DEB IP LIMITED, Derbyshire (GB)

(72) Inventors: Marcel Veeger, Goch (DE); Ute Wollenweber, Dusseldorf (DE); Markus Hemming, Oberhausen (DE)

(73) Assignee: DEB IP LIMITED, Denby, Derbyshire (GB)

( * ) Notice: Subject to any disclaimer, the term of this patent is extended or adjusted under 35 U.S.C. 154(b) by 0 days.

(21) Appl. No.: 14/374,760

(22) PCT Filed: Jan. 10, 2013

(86) PCT No.: PCT/EP2013/050370
§ 371 (c)(1),
(2) Date: Jul. 25, 2014

(87) PCT Pub. No.: WO2013/117375
PCT Pub. Date: Aug. 15, 2013

(65) Prior Publication Data
US 2015/0011451 A1    Jan. 8, 2015

(30) Foreign Application Priority Data

Feb. 6, 2012    (DE) .......................... 10 2012 201668

(51) Int. Cl.
| | | |
|---|---|---|
| C11D 1/72 | (2006.01) |
| C11D 9/20 | (2006.01) |
| C11D 7/14 | (2006.01) |
| C11D 17/08 | (2006.01) |
| C11D 3/37 | (2006.01) |
| A61K 8/73 | (2006.01) |
| A61K 8/37 | (2006.01) |
| A61Q 19/10 | (2006.01) |
| A61K 8/25 | (2006.01) |
| A61K 8/39 | (2006.01) |
| A61K 8/33 | (2006.01) |
| A61K 8/34 | (2006.01) |

(52) U.S. Cl.
CPC . *A61K 8/731* (2013.01); *A61K 8/25* (2013.01); *A61K 8/33* (2013.01); *A61K 8/34* (2013.01); *A61K 8/37* (2013.01); *A61K 8/39* (2013.01); *A61Q 19/10* (2013.01); *A61K 2800/31* (2013.01); *A61K 2800/591* (2013.01)

(58) Field of Classification Search
CPC .............. C11D 1/72; C11D 9/20; C11D 7/14; C11D 17/08; C11D 17/0026; C11D 3/124; C11D 3/1246; C11D 3/20983; C11D 3/37; C11D 17/0004
See application file for complete search history.

(56) References Cited

U.S. PATENT DOCUMENTS

| | | | |
|---|---|---|---|
| 5,891,449 A | 4/1999 | Daniel et al. | |
| 8,466,097 B2 | 6/2013 | Allef et al. | |
| 2004/0048756 A1* | 3/2004 | Haas et al. | 510/130 |
| 2011/0021398 A1* | 1/2011 | Allef et al. | 510/138 |
| 2014/0301896 A1* | 10/2014 | Brown | 422/28 |

FOREIGN PATENT DOCUMENTS

| | | |
|---|---|---|
| CA | 2687103 A1 | 11/2008 |
| DE | 4335933 A1 | 4/1995 |
| DE | 102007022693 A1 | 1/2009 |
| DE | 102008026051 A1 | 12/2009 |
| EP | 1504081 B1 | 2/2005 |
| WO | 2011051083 A2 | 5/2011 |

* cited by examiner

*Primary Examiner* — Charles Boyer
(74) *Attorney, Agent, or Firm* — Lynn C. Schumacher; Hill & Schumacher

(57) ABSTRACT

The present invention relates to compositions, particularly compositions with little or no water content, which can preferably be used as cleansing agents for the skin and/or hands, particularly for removing stubborn soiling of the skin.

14 Claims, No Drawings

ESSENTIALLY WATER-FREE PERSONAL CLEANSER CONTAINING ETHYL CELLULOSE

The present invention relates to compositions containing hydroxyethyl cellulose, particularly compositions with little or no water content, which can preferably be used as cleansing agents for the skin and/or hands, particularly for removing stubborn soiling of the skin.

Skin and hand cleansing agents are used extensively in industry, especially where stubborn stains occur, caused by paint, grease, oils, lubricants, metal dust, graphite, carbon black, etc. Such cleansing agents are known in particular as so-called heavy-duty hand cleansers (cf. H. Tronnier, J. Kresken, K. Jablonski, B. Komp, "Haut and Beruf," Grosse Verlag, Berlin, pp. 75-108 [1989]). Usually, these involve preparations which contain an abrasive, surfactant/surfactant mixtures, thickeners, and optionally additives for regulating the consistency of appearance, odour and stability, such as pigments, fragrances, stabilisers and preservatives. For particularly stubborn soiling, there are products for which the use of the above ingredients is not sufficient.

Organic solvents are then added to these preparations, such as aliphatic hydrocarbons, terpenes, carboxylic acid esters, particularly dibasic acid esters (DBE) of the dimethyl adipate, dimethyl glutarate, dimethyl succinate and di-n-butyl adipate or diisopropyl adipate type, such as those described in DE 43 35 933 A1.

In addition, reference should be made at this point to the so-called "waterless cleanser" available on the market whose good cleansing action is based primarily on the organic solvents mentioned above, in particular benzines, kerosenes, and short-chain paraffinic oils.

In view of the wide range of applications of heavy-duty hand cleansers, especially in the industrial sector and the fact that skin and hand cleansing soiling, when occurring in this sector, in many cases can be particularly stubborn and therefore not usually amenable to cleansing with conventional skin cleansers, for example in the painting industries, there remains a need for skin or hand cleansing agents which have a comparable cleansing action, such as products known in the prior art, for example, skin and hand cleansers containing DBE. As regards their cleansing action, such agents are in the so-called "heavy-duty hand cleanser range", i.e. virtually to be regarded in terms of their cleansing action as standard cleansers as a means of removing heavy soiling, with the result that the skin and hand cleansers without DBE as a skin cleansing enhancer must have at least a qualitatively comparable skin cleansing action to gain consumer acceptance for their intended purpose.

Despite the above-mentioned fact that carboxylic acid esters of the dimethyl adipate, dimethyl glutarate, dimethyl succinate and di-n-butyl adipate or di-isopropyl type have excellent effectiveness as a cleansing booster in skin and hand cleansing agents, the availability of this cosmetic raw material is limited in the marketplace and is often subject to large fluctuations, which naturally has a direct effect on the production cost of the end products. In addition, it has been shown that skin and hand cleansing agent formulations that contain DBE as a cleansing booster are often used additionally for stabilising in order to obtain marketable products. This contributes to an additional cost burden on the end products. Therefore, it would be advantageous to be able to use both skin and hand cleansing agent formulations containing DBE as a skin boosting reinforcing component and which are stabilised in a simple manner, as well as skin and hand cleansing agent formulations stabilised in the same way, which contain an alternative to the above-mentioned carboxylic acid esters of the DBE as cleansing boosters.

Accordingly, EP 1 504 081 B1, for example, contains a description of skin and hand cleansing agents based on fatty acid methyl esters. A disadvantage of the skin and hand cleansing products described in this document is that these skin and hand cleansers contain 10 to 80% by wt. of water. The result of this is not only a reduced cleansing performance, but there is a risk of hydrolysis and enhanced oxidation, in particular of the methyl esters in these aqueous formulations, which is accompanied by a reduction in the shelf life of such skin and hand cleansers.

With EP 1 504 081 B1 as the starting point, experiments aimed at producing low water content formulations, i.e. formulations with a water content of <10% by wt., led to unstable products or the products obtained formed no yield point in order, if abrasive beads were to be included optionally in the skin and hand cleansing agents, to prevent the beads from settling in the formulation, i.e. the stable incorporation of abrasive beads is significantly more difficult or impossible.

For soiling that cannot be removed satisfactorily by using the above-mentioned heavy-duty hand cleansers, organic solvents such as, for example, alkyl esters or diesters, are often added to the formulations, as described in DE 10 2008 026 051 A1. However, these solvent-based heavy-duty hand cleansers often show that they are insufficiently stable, especially in plastic packaging, so that after a short time they become inhomogeneous mainly through separation behaviour.

The task of the present invention, therefore, was to provide skin and hand cleansers, in particular for removing severe skin soiling, which have a good shelf life which is substantially independent of the material used for a storage container.

It has been found surprisingly that by adding hydrophobic cellulose derivatives to known formulations for skin and hand cleansers, the stability of these agents can be significantly improved, irrespective of the choice of packaging (glass, HDPE and LDPE bottles and dispenser bottles with an LDPE outer layer, bonding agents and a PA inner layer).

The skin and hand cleansing agents according to the invention have the advantage that their stability is almost independent of the choice of packaging (glass, HDPE and LDPE bottles and dispenser bottles with LDPE outer layer, bonding agents and a PA inner layer). Even after the expiration of a three-month stability test the skin and hand cleansers according to the invention have a homogeneous texture.

The compositions according to the invention have the additional advantage that, if abrasive beads are incorporated optionally in the skin and hand cleansers, the beads are prevented from settling in the formulation.

The compositions according to the invention are simple to manufacture in terms of production methods.

Compositions according to the invention preferably have a flash point >100° C., and preferably have a vapour pressure at 20° C. of <0.01 hPa. In this way it can be ensured that the heavy-duty hand cleanser does not ignite in production shops with high ambient temperatures and that residual solvent remains in the composition, so that even after prolonged storage (3 months) the effectiveness of the composition and its consistency will not be diminished, or only to an insignificant degree.

By using the composition according to the invention, it is possible to use heat-treated instead of bleached (walnut) shell flour, so that the composition according to the invention can be or is produced in an overall environmentally friendly manner.

Compositions according to the invention, the process for their preparation and the use of the compositions are described below by way of example without the invention being restricted to these exemplary embodiments. Where ranges, general formulas or compound classes are given below, these are intended to include not only the corresponding ranges or groups of compounds that are explicitly mentioned but also all sub-ranges and subgroups of compounds that can be obtained by extracting individual values (ranges) or compounds. If documents are cited in the present description, then their content, particularly with respect to the referenced issues, is intended to belong fully to the disclosure content of the present invention. If the data below are given as a percentage, unless otherwise stated, the information is expressed as a % by wt. If averages are given below, unless otherwise specified, they are expressed as the numerical average. If material properties, such as viscosities or the like, are stated, unless otherwise specified, the material properties are those at 25° C.

The composition according to the invention, particularly one suitable for the cleansing of the skin and/or hands, is characterised in that it contains the components:

a.) at least one alkyl ester and/or diester,
b.) 0 to 40% by wt. of at least one surfactant selected from the group of fatty alcohol ethoxylates,
c.) at least one thixotropic agent and at least one hydrophilic, pyrogenic silicic acid,
d.) 0 to 30% by wt. of one or more abrasives,
e.) 0 to 5% by wt. of at least one physiologically compatible carbonic acid ester
f.) 0 to <10% by wt. water,
g.) optionally one or more viscosity-forming agents,
h.) optionally further cosmetic supplements, additives and/or active ingredients, and
i.) 0.1 to 20% by wt. of hydroxyethyl cellulose in which 1.0 to 2.9 3'-OH groups on average per D-glucopyranose unit present are replaced by ethoxy groups, wherein the sum of the components a.) to i.) add up to 100% by wt. relative to the composition.

The alkyl esters of component a.) employed according to the invention may be, for example, synthetically produced fatty acid alkyl esters, which can be obtained as reaction products of fatty acids with aliphatic alcohols, or alternatively also during the transesterification of natural or synthetic fats and oils, wherein, in fatty acid alkyl esters derived from naturally occurring oils, these are treated or cleaned, preferably industrially, for cosmetic use. Fatty acid alkyl esters of component a.) preferably have the general formula (I)

$$R^1CO—OR^2 \qquad (I)$$

in which $R^1CO$ stands for a linear or branched, saturated and/or unsaturated acyl radical containing 6 to 22, in particular 8 to 22, preferably 12 to 22 carbon atoms and $R^2$ for an alkyl radical having 1 to 8 carbon atoms, in particular for an alkyl radical having 1 to 4 carbon atoms, and particularly preferably stands for a methyl radical.

Preferred fatty acid alkyl esters are, for example, methyl, ethyl, propyl, isopropyl, n-butyl, isobutyl, tert-butyl, pentyl, hexyl, or 2-ethylhexyl ester, preferably methyl or isopropyl ester, preferably methyl ester, in particular those of caproic acid, caprylic acid, capric acid, lauric acid, myristic acid, palmitic acid, palmitoleic acid, stearic acid, isostearic acid, oleic acid, elaidic acid, linoleic acid, linolenic acid, gadoleic, arachidonic acid, behenic acid and erucic acid and the technical mixtures thereof.

According to the invention, preferred fatty acid methyl esters, fatty acid isopropyl esters and fatty acid 2-ethylhexyl esters are, for example, available from the Cognis company under the trade name TEXAPRINT®.

In particular, such fatty acid esters also are used according to the invention as component a.), which can be derived from so-called "vegetable oils," such as, for example, the vegetable oil esters obtainable with an alcohol by esterification, for example, of soybean oil, sunflower oil, coconut oil or canola oil.

Particularly preferably, the fatty acid methyl esters are used as component a.), which can be obtained for example under the name Edenor ME SU from Cognis also.

The component a.) can also be diesters, especially those with the general formula (II), $$R^3OOC—X—COOR^4 \qquad (II)$$

in which X stands for a linear or branched, saturated and/or unsaturated alkyl radical with 0 to 20, preferably 0 to 6 carbon atoms and $R^3$ and $R^4$ equally or differently stand for an alkyl radical having 1 to 8 carbon atoms, especially for a methyl radical.

Preferred diesters are particularly dimethyl adipate, dimethyl glutarate, dimethyl succinate (DBE), di-n-butyl adipate, diisopropyl or dimethyl-2-methyl-glutarate.

The alkyl esters and/or diesters of component a.) can be used alone or as mixtures, wherein, in particular, mixtures of this type are preferred which have only methyl esters and/or dimethyl esters as component a.).

The compositions according to the invention preferably contain from 5 to 90% by wt., preferably 10 to 65% by wt., and particularly preferably 25 to 65% by wt. of component a.) based on the total composition.

The fatty alcohol ethoxylates which can be used as component b.) preferably have the general formula $$R—O—(CH_2—CH_2—O)_nH$$

where
R=a saturated, unsaturated, branched or unbranched alkyl radical,
n=integer from 1 to 11.

Alkyl radicals preferably used, whether saturated, unsaturated, branched or unbranched, are R=$C_6$ to $C_{18}$, particularly $C_{10}$ to $C_{16}$ and more preferably $C_{11}$ to $C_{14}$, preferably wherein n=3 to 6, more particularly n=5 to 7.

The content of component b.) in the composition according to the invention is preferably 1 to 40% by wt., preferably 5 to 30 and particularly preferably 10 to 30% by wt., based on the total composition. In a preferred embodiment, the compositions according to the invention contain from 5 to 35% by wt., based on the composition, of laureth-6 as component b.).

According to the invention, a thixotropic is understood to mean an agent which is suitable for increasing the yield point of a dispersed system, such as a cosmetic formulation containing an abrasive medium. Such thixotropic agents are, for example, known for a variety of applications as "rheological additives", in particular for the manufacture of lacquers and paints, in which they act as a so-called "anti-settling agents". This involves, for example, bentonite, kaolin, alginic acid, as well as the industrially important $SiO_2$ modifications such as silica and diatomaceous earth and silica gels.

In cosmetic formulations such thixotropic agents are also responsible for the formation of a solid gel, a so-called "house of cards structure". This is the case particularly in cosmetic formulations containing polar organic media. Such a "house of cards structure", however, does not develop in skin and hand cleansers containing ethoxylated fatty alcohols as cleansing boosters, and the disruption is so great that there is no guarantee that such a cosmetic formulation can be stabilised.

Surprisingly, it has now been found that such systems can be stabilised if these cosmetic formulations, in particular skin and hand cleansers, contain a hydrophilic fumed silica as well as a thixotropic agent. The measurement of the contact angle between water and the surface of the silica serves as the measure of the hydrophilic surface. The size of the contact angle between water and solid is dependent on the interaction between the substances at the contact area and the smaller this interaction, the greater is the contact angle. If the contact angle is less than 90°, hydrophilic surfaces are present [Thieme Römpp Online, document reference RD-08-02255, Georg Thieme Verlag, 2012]. The contact angle can be determined by a contact angle meter from Krüss GmbH.

In the case of hydrophilic fumed silicas, they should preferably be very finely divided and thus homogeneously incorporated in the final formulation, i.e. $SiO_2$ modifications that have been prepared by flame hydrolysis. The material is wetted by water and can be dispersed in water. The hydrophilic fumed silicas of component c.) employed in accordance with the invention are available for example under the trade name AEROSIL® from Evonik Industries AG and are used, amongst other things, in paints and coatings for optimal rheological adjustment or for thickening of non-polar liquids, such as fats and oils.

The inventive compositions preferably contain >0.1% % by wt., particularly 0.5-5.0% by wt. of hydrophilic fumed silica, based on the total composition, wherein the silicas available from Evonik Industries AG under the trade name AEROSIL® 200 are particularly preferred.

The thixotropic agents of component c.) are contained in the compositions according to the invention preferably in amounts from 0.5 to 10% by wt., preferably from 0.5 to 7.5 and particularly preferably from 2 to 6% by wt. based on the total composition. Preferred thixotropic agents are organophilic and/or hydrophobic layer silicates, in particular bentonite, preferably those in which the inorganic cations of natural bentonites, such as Na-bentonite, have been replaced by organic radicals, especially quaternary ammonium cations, such as in the bentonites sold by Rockwood Clay Additives, Moosburg, Germany, under the trade name TIXOGEL®.

Such organic bentonites can be characterised, for example, by determining their loss on ignition at 1000° C., which can be regarded as a meaningful parameter for the ratio of organic radical to bentonite. The loss on ignition in this case comprises the total organic proportion of the bentonite and the chemically bound water of the bentonite (approximately 8% for pure bentonite). It has now been found that bentonites having an ignition loss of up to 30% by wt. in combination with a hydrophilic fumed silica in an anhydrous solvent-based skin and hand cleanser provide sufficient stability so that product instabilities were no longer seen. Preferably, the organobentonites have a loss on ignition of at least 8% by wt., preferably at least 10% by wt.

According to the invention, stearalkonium bentonites, according to INCI nomenclature, that are particularly preferred are those with a loss on ignition of a maximum of 29%, such as stearalkonium bentonites, obtainable under the trade name TIXOGEL® LG-M from Rockwood Clay Additives GmbH, Moosburg, Germany, and exhibiting a loss on ignition of about 28% by wt. Such stearalkonium bentonites are contained in the compositions according to the invention preferably in an amount of >0.5% by wt., based on the total composition, and more preferably >2% by wt.

It was surprising that such stearalkonium bentonites, exhibiting an ignition loss of up to 29% such as those stearalkonium bentonites available under the trade name TIXOGEL® LG-M, and have been used up to now in nail polishes in particular for stabilisation of colour pigments, can be used now for stabilising anhydrous or low-water compositions, particularly for skin and hand cleansers.

The skin and hand cleansers according to the invention produce a very good cleansing action, but nonetheless the skin and hand cleansers may optionally contain abrasives for certain cleansing applications as optional component d.).

The proportion of abrasive or abrasives in the composition is then preferably from >0 to 30% by wt., preferably 5 to 30% by wt., and particularly preferably from 5 to 25% by wt. based on the composition. As abrasives, the compositions according to the invention for hand and/or skin cleansers have all known abrasives. Abrasives that can be used include inorganic abrasives such as sand, pumice, calcium carbonate or kaolin as well as organic abrasives. Organic abrasives that can be used, for example, include synthetic abrasives based on polyethylene or polyurethane, water-swellable particulate organic polymers, abrasives based on natural kernel, husk and/or shell flours, especially walnut shells, almond shells, hazelnut shells, olive pit, apricot pit, cherry pit and corn flour or any mixtures of these husk and kernel flours or wax pearls, such as jojoba wax. As regards husk and/or kernel flours, those known from prior art can be used, such as flours bleached with hydrogen peroxide or heat-treated flours. Heat-treated flours are used preferably, particularly those described in WO 2011/051083. Preferably, the composition according to the invention has, as abrasives, walnut shell flour, and particularly preferably heat-treated walnut shell flour, particularly that as is described in WO 2011/051083. It may be advantageous if two or more of the above abrasives are present as a mixture in the composition according to the invention as component d.).

In a particularly preferred embodiment of the invention, the composition according to the invention contains, as abrasives, alone or in combination with other abrasives, preferably in combination with walnut shell flour, water-swellable particulate organic polymers of natural and/or synthetic origin, which, in addition to their action as a cleansing booster, can prevent coagulation and re-deposition of dissolved or emulsified dirt when applying the agent.

Descriptions appear in DE 37 36 970, for example, of these types of particulate organic polymers, insoluble in water but more often simply water-swellable, derived from natural and/or synthetic origins and used as abrasives for skin and hand cleansing agents. These concern polymerisates based on modified natural substances, or based on synthetic products wherein the water insolubility is achieved essentially by cross-linking. The term 'polymerisates' includes both the homopolymers as well as the copolymers and terpolymers.

Suitable organic polymers based on modified natural substances are, for example, those products based on starch and cellulose, which may be modifiable preferably by grafting with acrylic derivatives. These acrylic derivatives are, for example, (meth)acrylic acid and salts thereof, (meth)acrylonitrile, (meth)acrylamide and (meth)acrylic esters, as well as the partial hydrolysis products of these acrylic derivatives.

The homopolymers and copolymers, in particular the aforementioned acrylic derivatives, should be cited as synthetic organic polymers. This involves essentially cross linked polyacrylic acids or cross linked starch/acrylic acid graft copolymerisates, in which the carboxyl groups can be neutralised partially with sodium or potassium ions. Regarding comonomers, the polymerisates can contain acrylamido propanesulfonic acid, vinylphosphonic acid, vinylsulfonic acid, dialkylaminoalkyl (meth)acrylates, dialkylamino (meth)acrylamides, as well as the quaternised forms of the two aforementioned basic comonomers. Furthermore, polyurethanes are also suitable.

According to the invention, abrasives are preferably in the form of water-swellable polymers obtained by polymerisation of the components aa.) 55 to 99.95% by wt. of monoethylenically unsaturated carboxyl group-containing monomers,
bb.) 0.05 to 5.0% by wt. of at least one cross-linking agent,
cc.) 0 to 40% by wt. of further monomers copolymerisable with a.),
dd.) 0 to 30% by wt. of a water-soluble graft base,
and the components aa.) to dd.) add up to 100% by wt., wherein the resulting polymerisates may optionally be post cross-linked at least once.

In this arrangement, in particular monoethylenically unsaturated $C_3$ to $C_{10}$ monocarboxylic acids and their alkali metal and/or ammonium and/or amine salts are cited as monoethylenically unsaturated carboxyl-containing monomers of component aa.). These monomers include, for example, acrylic acid, methacrylic acid, dimethacrylic acid, ethylacrylic acid, crotonic acid, isocrotonic acid, vinylacetic acid, and allylacetic acid. From this group, acrylic acid, methacrylic acid or their alkali metal or ammonium salts or mixtures thereof are used as preferred monomers wherein acrylic acid as well as their sodium, potassium or ammonium salts are particularly preferably as monomers.

Other monoethylenically unsaturated carboxyl group-containing monomers are also the monoethylenically unsaturated $C_4$ to $C_8$ dicarboxylic acids, their anhydrides or their alkali and/or ammonium and/or amine salts. Suitable dicarboxylic acids are, for example, maleic acid, fumaric acid, itaconic acid and methylenemalonic acid, wherein maleic acid, maleic acid anhydride, itaconic acid, itaconic anhydride, as well as the corresponding sodium, potassium or ammonium salts of maleic or itaconic acid are preferred.

Monoethylenically unsaturated carboxyl group-containing monomers are also the hydrolyzates of (meth)acrylonitrile copolymers and of starch-(meth)acrylonitrile graft copolymers, hydrolysates of (meth)acrylamide copolymers and saponification products of (meth)acrylic acid copolymers with ethylenically unsaturated esters as carboxylate group-containing polymers.

The acidic, polymerised monomer components of the water-swellable polymerisates are preferably neutralised to at least 25 mole %, and preferably to at least 50 mole %, and more preferably to at least 75 mol %, and are present, as described above, for example, as sodium, potassium, or ammonium salt or mixtures thereof.

Usually compounds are used as a cross-linking agent of component bb.), wherein the compounds have at least two ethylenically unsaturated double bonds or one ethylenically unsaturated double bond and a group reactive functionally to acid groups or a plurality of groups reactive functionally to acid groups. Preferred cross linking agents are those containing at least two ethylenically unsaturated double bonds, such as methylenebisacrylamide or -methacrylamide or ethylenebisacrylamide, and also esters of unsaturated mono-or polycarboxylic acids of polyols, such as diacrylates or triacrylates, e.g. butanediol or ethylene glycol diacrylate or methacrylate, trimethylolpropane triacrylate, as well as their alkoxylates with preferably 1 to 30 mols of ethylene oxide, and furthermore, allyl compounds and their alkoxylates such as allyl (meth)acrylate, allyl $(EO)_{1-30}$ (meth) acrylate, triallyl cyanurate, maleic acid allyl ester, polyallyl ester, tetraalloxyethane, di-and triallyl amine, tetraallylethylenediamine, allyl esters of phosphoric acid or phosphorous acid.

Compounds meriting mention and at least having a group reactive functionally to acid groups, include, for example, the n-methylol compounds of amides, such as methacrylamide or acrylamide, and the ethers derived therefrom, as well as di- and polyglycidyl compounds.

The cross linking agents may be used alone or in combination in amounts of 0.05-5.0% by wt., preferably 0.05 to 2.0 weight % by wt., and particularly preferably from 0.1 to 1.0 weight % by wt., based on the monomers.

In addition to the monoethylenically unsaturated carboxyl-containing monomers and the cross linking agents (component aa.) and bb.)), it is possible, as an option in the preparation of these water-swellable polymerisates, to include as component cc.) other comonomers, substantially soluble in an aqueous monomer solution, for the purpose of modifying the properties. Such comonomers may be, for example, (meth)acrylamide, (meth)acrylonitrile, vinyl pyrrolidone, vinyl acetamide, 2-acrylamido-2-methylpropanesulfonic acid, vinylsulfonic acid, (meth)allylsulfonic acid, hydroxyethyl acrylate, alkyl polyethylene glycol (meth)acrylates, alkylaminoalkyl (meth)acrylates, alkylaminopropylacrylamides, acrylamidopropyl trimethyl ammonium chloride or mixtures thereof. Such comonomers should not exceed a proportion of 40% by wt. because they may interfere with the swelling properties of the resulting water-swellable polymerisate.

In addition, the water-swellable polymerisates can contain water-soluble polymers as component dd.) as a grafting base, held optionally in amounts up to 30% by wt. These include, amongst other things, partially or fully hydrolysed polyvinyl alcohols, polyacrylic acids, polyglycols or mixtures thereof, polysaccharides such as starch or starch derivatives, cellulose or cellulose derivatives but also polycarboxypolysaccharides. The latter are derived from either from polysaccharides which contain no carboxyl groups naturally, and are provided by subsequent modification with carboxyl groups or they contain carboxyl groups naturally and can be provided subsequently with further carboxyl groups by modification if necessary.

The first group of polysaccharides include, for example, starch, amylose, amylopectin, cellulose and polygalactomannans such as guar and locust bean gum, while the second group includes, for example, xanthanes, alginates, gum arabic etc.

The carboxyl groups are, as mentioned already, either present due to the molecular structure provided naturally, for example, due to uronic acid units in the polysaccharide molecule or are incorporated by subsequent modification with carboxyl group-containing reagents or are generated by oxidation reactions. Among the polycarboxypolysaccharides wherein the carboxyl groups are incorporated by subsequent modification, carboxylalkyl derivates are preferred, especially the carboxymethyl derivatives. Among the polycarboxypolysaccharides wherein the carboxyl groups are produced by oxidation of the polysaccharide molecule, oxidised starches and derivatives thereof are preferred in particular.

Polycarboxypolysaccharides can be modified in addition to the carboxyl groups with other groups, in particular those which improve the water-solubility, for example, hydroxyalkyl, especially hydroxyethyl groups, and phosphate groups.

Particularly preferred polycarboxypolysaccharides are carboxymethyl guar gum, carboxylated hydroxyethyl- or hydroxypropyl cellulose, carboxymethyl cellulose and carboxymethyl starch, oxidised starch, carboxylated starch phosphate, xanthane gum and mixtures of the individual polycarboxypolysaccharides.

In particular, carboxymethyl cellulose is preferably used.

Polycarboxypolysaccharide derivates with low and high degrees of carboxyl substitution can be used. However, they usually have an average carboxyl substitution degree in the range of 0.3 to 1.5, so that polycarboxypolysaccharide derivates with a substitution degree in the range of 0.4 to 1.2 are preferably used.

With regard to component dd.), it should be noted that the molecular weights of the polymers added as graft bases are preferably adapted to the circumstances of the polymerisation. It may, for example, be required in the case of an aqueous polymerisation solution that only low or medium molecular weight polymers are used, as this factor plays a minor role only in the suspension polymerisation.

It is known also that water-swellable polymerisates can be improved in their property profile by the process of subsequent surface cross-linking. During such post cross-linking, the carboxyl groups of the polymer molecules are cross-linked at the surface of water-swellable polymer particles with cross-linking agents at elevated temperatures. For post cross-linking agents, compounds are used which possess at least two functional groups capable of cross-linking the functional groups of the polymerisates at the surface of the polymer particles. In this instance, alcohol, amino, aldehyde, glycidyl, epichloro- and isocyanate functions are preferred, wherein cross-linker molecules with a plurality of different functions, as well as polyvalent metal salt compounds, can be used. Typical examples of post cross-linking agents include ethylene glycol, diethylene glycol, triethylene glycol, glycerin, polyglycerin, propylene glycol, diethanolamine, triethanolamine, sorbitan fatty acid esters, trimethylolpropane, pentaerythritol, polyvinyl alcohol, sorbitol, ethylene carbonate, propylene carbonate, polyepoxides such as, for example, ethylene glycol diglycidyl ether, aziridines and polyisocyanates. It is preferable to use ethylene carbonate as a post cross-linker. The post cross-linking agents are used in an amount of 0.01 to 10% by wt., preferably 0.1 to 5% by wt., more preferably from 0.1 to 1.5% by wt. based on the polymerisate to be post cross-linked, wherein the surface post cross-linking can be repeated several times as appropriate.

In the preparation to be used according to the invention, water-swellable polymerisates containing carboxylate groups can be used as carboxyl group-containing monomers, for example, acrylic acid, methacrylic acid, vinylacetic acid, maleic acid or mixtures thereof. The use of acrylic acid alone or mixtures thereof is preferred.

In addition to polymerisates, which are obtained by cross-linking polymerisation of partially neutralised acrylic acid, polymerisates may be used that include additional proportions of graft-polymerised starch and/or polyvinyl alcohol.

Such water-swellable solid particles acting as abrasives can be contained in the skin and hand cleanser according to the invention, alone or with one or more of the above cosmetic abrasives up to 30% by wt., based on the total composition of the skin and hand cleanser, preferably 1 to 25% by wt., particularly preferably 1 to 15% by wt.

According to the invention, preferred water-swellable abrasives are those obtainable from Evonik Industries, Krefeld (Germany) under the trade name Favor® T 5056 F. Particularly preferred as component d.) are water-swellable polymers acting as abrasives and heat-treated walnut shell flour which can be obtained also from Evonik Industries, Krefeld site, under the name ASTOPON®.

Furthermore, the compositions according to the invention may consist, optionally as component e.), of 0 to 5% by wt., preferably 0.5 to 2.5% by wt. of at least one physiologically compatible ester of carbonic acid, that is, of a carbonic acid ester which is acceptable for cosmetic applications. Preferably, the composition according to the invention contains propylene carbonate as the physiologically acceptable acid ester.

In the case of anhydrous compositions, especially skin and/or hand cleansers or use of stearalkonium bentonites with a loss on ignition of a maximum of 30% as a thixotropic agent, these carbonic acid esters such as propylene carbonate act not only as activators but, in addition to stabilising the formulation, also provide an anti-settling effect in the formulations according to the invention, especially at room temperature (20° C.) and in cold storage (4° C.), which could not be achieved by other stearalkonium bentonites with a loss on ignition of >30%.

The skin and hand cleansing agents according to the invention are preferably anhydrous or have a low moisture content and contain only 0 to <10% by wt. as component f.).

Particularly preferred skin and hand cleansing agents are anhydrous and contain at least 10% by wt. of the corresponding methyl esters of the alkyl esters and/or diesters as component a.) and at least 5% by wt. of fatty alcohol ethoxylate as component b.), preferably laureth-6 according to the invention.

The skin and hand cleansers according to the invention comprise, as a thickening agent i.), hydroxyethyl cellulose, in which on the average preferably from 1.5 to 2.9, preferably from 2.0 to 2.7 and preferably from 2.5 of the 3'-OH groups present per d-glucopyranose unit are replaced with ethoxy groups. Suitable hydroxyethyl celluloses can be obtained for example from The Dow Chemical Company under the designation ETHOCEL®. Especially suitable is the product ETHOCEL® Standard 20 industrial from The Dow Chemical Company.

The content of hydroxyethyl cellulose in the skin and/or hand cleansers according to the invention, in which on average 1.0 to 2.9 of the 3'-OH groups present per d-glucopyranose unit are substituted by ethoxy groups, comprises preferably 1 to 10% by wt., preferably 2 to 5% by wt. and more preferably 3 to 4% by wt. based on the total mass of the skin and/or hand cleanser according to the invention.

In addition, the skin and hand cleansers according to the invention can also optionally contain one or more viscosity-forming agents as component g.), examples including polysaccharides, such as cellulose, guar gum and/or xanthanes, modified polysaccharides, preferably cellulose ethers, carboxyalkyl cellulose and/or hydroxyalkyl celluloses, preferably hydroxyethyl cellulose and/or inorganic electrolytes, preferably sodium chloride and/or magnesium sulphate, with the proviso that these viscosity-forming agents of component i.) are different.

Furthermore, the skin and hand cleansers according to the invention can optionally contain further cosmetic supplements, additives and/or active substances, such as pH regulators, stabilisers, preferably cetearyl alcohol and/or hydrogenated castor oils, such as trihydroxystearin, perfumes, preservatives, preferably organic acids, and antioxidants, such as, for example, vitamin E acetate, as component h.). Preferably oily or aqueous care components may also be used, such as bisabolol, aloe vera, panthenol, sodium PCA, jojoba oil, creatine, etc. in order to reinforce the care effect. The same applies to the optional additional use of care components such as hydrophilic emollients, such as partial glycerides or oils, through which a significant increase in skin care effect can be observed. Very good care effects are achieved, for example, with polyglyceryl partial esters as have been described in DE 10 2007 022 693.

Furthermore, conventional cosmetic superfatting or oil-replenishment agents such as isooctyl stearates, for example, can be used in order to minimise the skin drying effects, in particular by minimising the use of the incorporated solvents.

The additional use of hydrogenated castor oil is particularly advantageous, where appropriate, such as, for example, RHEOCIN® (Rockwood Clay Additives, Moosburg, Germany) or other waxes as stabilising agents, preferably 0.5 to 5% by wt., more preferably 0.5 to 3% by wt., based on the total composition of the cleansing agent, in particular not only to achieve stabilisation at different storage temperatures but also to achieve the necessary thermal stability of the cosmetic formulations, in particular at 40° C.

In this context it should be emphasised that stable and storable skin and hand cleansing agents based on alkyl esters with a water content of <10% by wt., based on the total composition, can be obtained only when these agents according to the invention comprise a synergistic combination of at least one thixotropic agent with at least one hydrophilic, fumed silica as a component.

Cosmetic formulations containing stearalkonium bentonite and hydrogenated castor oil could not stabilise the overall system sufficiently.

Only by the addition, according to the invention, of a hydrophilic silicic acid such as AEROSIL® 200 was it possible to achieve sufficient stabilisation, in particular at room temperature.

The production of the compositions according to the invention, especially skin and hand cleansers, preferably heavy-duty hand cleansers, is preferably carried out by means of known devices in a batch or continuous process in which the skin and hand cleansing agents are preferably obtained as creamy or as fluid viscous pastes. Suitable devices are temperature-controlled vessels with a stirrer, and continuous mixers such as extruders and dispersing agents.

The compositions according to the invention may be used preferably, for example, as a skin and/or hand cleanser, especially as a low-water or water-free skin and/or hand cleanser. Particularly preferably, the composition according to the invention is used as a skin and/or hand cleanser for removing stubborn soiling.

One example of the use of the compositions according to the invention as a skin and/or hand cleanser is preferably where, first, the composition is spread on the skin without water and then wiped off without water using a cloth, preferably a disposable item of paper, plastic or woven fabric, etc. However, an application with the aid of water is also possible. In this method, the product is washed off along with the soiling.

The compositions according to the invention can be used in particular for the removal of coarse contaminants adhering strongly to the skin such as grease, oils and other lubricants, paints, tar, graphite, carbon black, pigments and similar substances, such as those occurring, for example, in the industrial and public sectors, in crafts, agriculture as well as in the household. Particularly advantageous are the compositions according to the invention used in the cleansing of stubborn lacquer contamination, wherein in this case the cleansing agent should contain at least 10% by wt. of component b.) based on the composition, in particular of fatty alcohol ethoxylates.

In the examples given below, the present invention is described by way of example, without intending to limit the invention, whose breadth of application derives from the description and the claims, to the embodiments mentioned in the examples.

EXAMPLES

Stability Testing

The stability testing was carried out according to the IFSCC Monograph 1992 Number 2 "The Fundamentals of Stability Testing" where, in Chapter IV, page 8, "Standard Test Conditions" are described which served as the basis for the stability tests performed. The standard test conditions in chapter IV inter alia were used over a period of 3 months at 4° C., RT and 40° C.

Embodiment Examples

Skin and hand cleansing agents were prepared according to the compositions shown in Table 1 by homogeneous dispersion of all components at room temperature, ensuring that the organic gelling agent obtainable under the name RHEOCIN® from Rockwood Clay Additives, Moosburg, Germany was incorporated into the formulation at at least 40° C.

The agents were characterised with respect to their cleansing action on a lacquer and in terms of their stability.

Examples of compositions of the skin and hand cleansers according to the invention are shown in the following Table 1 under the formulations 1 to 4. Non-inventive comparative formulations appear as formulations 5 and 6.

TABLE 1

| | All formulation examples in % by wt | | | | | |
|---|---|---|---|---|---|---|
| | 1 | 2 | 3 | 4 | 5 | 6 |
| Fatty acid alkyl esters: methyl oleate | 51.35 | 52.35 | 53.29 | — | 44.1 | — |
| Fatty alcohol ethoxylate (Rewopal ® LA6) | 17.00 | 17.00 | 17.00 | 17.00 | 17.00 | 19.50 |
| Stearalkonium (TIXOGEL ® LG-M) | 3.00 | 3.00 | 2.25 | 3.00 | 4.00 | — |
| Ethocel Standard 20 industrial | 4.00 | 4.00 | 3.00 | 4.00 | — | 4.00 |
| Hydrophilic silicic acid (AEROSIL ® 200) | 2.50 | 1.50 | 2.50 | 2.50 | 2.50 | 2.50 |
| RHEOCIN ® stabiliser | — | — | — | — | 1.50 | 1.50 |
| Isopropyl Myristate (Tegosoft ® M) | — | — | — | 53.25 | — | 52.50 |
| Sodium tripolyphosphate | — | — | — | 2.00 | — | 2.00 |
| Favor ® T 5056 F | 4.00 | 4.00 | 4.00 | 4.00 | 4.00 | 4.00 |
| Propylene carbonate | 0.75 | 0.75 | 0.56 | 0.75 | 1.00 | — |
| Walnut shell flour (heat treated) | 12.00 | 12.00 | 12.00 | 12.00 | 12.00 | 12.50 |

TABLE 1-continued

| | All formulation examples in % by wt | | | | | |
|---|---|---|---|---|---|---|
| | 1 | 2 | 3 | 4 | 5 | 6 |
| Titanium dioxide | 1.00 | 1.00 | 1.00 | 1.00 | 1.00 | 1.00 |
| Isooctyl stearate (superfatting agent) | 3.90 | 3.90 | 3.90 | — | 3.90 | — |
| Perfume | 0.50 | 0.50 | 0.50 | 0.50 | 0.50 | 0.50 |
| City water | — | — | — | — | 8.50 | — |
| Total | 100.00 | 100.00 | 100.00 | 100.00 | 100.00 | 100.00 |
| Stability at 4° C./20° C./40° C. | stable | stable | stable | stable | unstable | unstable |

As shown in Table 1 it can be seen that the comparison formulations, which do not have all of the features essential to the invention, are not stable at all tested temperatures, whereas the compositions according to the invention are stable under the specified test conditions.

The invention claimed is:

1. Composition, particularly suitable for cleansing skin and/or hands containing the following components:
   a.) at least one alkyl ester and/or diester,
   b.) 0 to 40% by wt. of at least one surfactant selected from the group of fatty alcohol ethoxylates,
   c.) at least one thixotropic agent and at least one hydrophilic, pyrogenic silicic acid,
   d.) 0 to 30% by wt. of one or more abrasives,
   e.) 0 to 5% by wt. of at least one physiologically compatible carbonic acid ester
   f.) 0 to <10% by wt. water,
   g.) optionally one or more viscosity-forming agents,
   h.) optionally further cosmetic supplements, additives and/or active ingredients, and
   i.) 0.1 to 20% by wt. of hydroxyethyl cellulose in which 1.0 to 2.9 of the three-OH groups on average per d-glucopyranose unit present are replaced by ethoxy groups,
   wherein the sum of the components a.) to i.) total 100% by wt. relative to the composition.

2. Composition in accordance with claim 1, characterised in that it has, as component a.), fatty acid esters with the general formula (I), namely $$R^1CO\text{—}OR^2 \qquad (I)$$

in which $R^1CO$ stands for a linear or branched, saturated and/or unsaturated acyl radical containing 6 to 22 carbon atoms and $R^2$ for an alkyl radical having 1 to 8 carbon atoms.

3. Composition in accordance with claim 1, characterised in that it has, as component a.), diesters with the general formula (II), namely $$R^3OOC\text{—}X\text{—}COOR^4 \qquad (II)$$

in which X stands for a linear or branched, saturated and/or unsaturated alkyl radical with 0 to 20 carbon atoms and $R^3$ and $R^4$ equally or differently stand for an alkyl radical having 1 to 8 carbon atoms.

4. Composition in accordance with claim 3, characterised in that it contains alkyl esters and/or diesters of component a.) in the proportion 5 to 70% by wt. based on the total composition.

5. Composition in accordance with claim 4, characterised in that it contains as component b.) at least one fatty alcohol ethoxylate with the general formula $$R\text{—}O\text{—}(CH_2\text{—}CH_2\text{—}O)_nH$$

where
   R=a saturated, unsaturated, branched or unbranched alkyl radical,
   n=integer from 1 to 11.

6. Composition in accordance with claim 5, characterised in that it contains as component b.) at least one fatty alcohol ethoxylate in the proportion 1 to 35% by wt. based on the total composition.

7. Composition in accordance with claim 6, characterised in that it contains laureth-6 as a fatty alcohol ethoxylate of component b.) in the proportion 5 to 35% by wt. based on the total composition.

8. Composition in accordance with claim 7, characterised in that it contains as component c.) 0.5 to 10% by wt., based on the total composition, of at least one thixotropic agent and >0.1% by wt., based on the total composition, of at least one hydrophilic, pyrogenic silicic acid.

9. Composition in accordance with claim 8, characterised in that the thixotropic agent of component c.) is an organophilic and/or hydrophobic layered silicate.

10. Composition in accordance with claim 9, characterised in that it has 5 to 30% by wt. of one or more abrasives as component d.).

11. Composition in accordance with claim 10, characterised in that it has, as abrasives of component d.), sand, pumice, calcium carbonate, kaolin, synthetic abrasives based on polyethylene or polyurethane, abrasives based on natural kernel, husk and/or shell flours, especially walnut shells, almond shells, hazelnut shells, olive pit, apricot pit, cherry pit and corn flours or any mixtures of these husk and kernel flour and/or wax pearls.

12. Composition in accordance with claim 11, characterised in that it is water-free.

13. Application of a composition in accordance with claim 1 as a skin and hand cleansing agent.

14. Application in accordance with claim 13, characterised in that the composition is used as a skin and/or hand cleansing agent for removing stubborn soiling.

* * * * *